(12) United States Patent
Langer et al.

(10) Patent No.: US 8,901,300 B2
(45) Date of Patent: Dec. 2, 2014

(54) TETRAAZAPYRENE COMPOUNDS AND THEIR USE AS N-TYPE SEMICONDUCTORS

(75) Inventors: Nicolle Langer, Heppenheim (DE); Sonja Geib, Dossenheim (DE); Susanne Martens, Loerrach (DE); Lutz Gade, Nussloch (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/995,761

(22) PCT Filed: Feb. 16, 2012

(86) PCT No.: PCT/IB2012/050702
§ 371 (c)(1),
(2), (4) Date: Jun. 19, 2013

(87) PCT Pub. No.: WO2012/110970
PCT Pub. Date: Aug. 23, 2012

(65) Prior Publication Data
US 2013/0324723 A1 Dec. 5, 2013

Related U.S. Application Data

(60) Provisional application No. 61/444,157, filed on Feb. 18, 2011.

(51) Int. Cl.
| | | |
|---|---|---|
| C07D 487/04 | (2006.01) | |
| C09B 49/12 | (2006.01) | |
| C09K 11/06 | (2006.01) | |
| C07D 487/06 | (2006.01) | |
| H01L 51/00 | (2006.01) | |
| C09B 57/00 | (2006.01) | |
| H01L 51/05 | (2006.01) | |
| H01L 51/50 | (2006.01) | |

(52) U.S. Cl.
CPC ......... *H01L 51/0072* (2013.01); *H01L 51/0541* (2013.01); *C09K 2211/1011* (2013.01); *C09B 49/12* (2013.01); *C09K 11/06* (2013.01); *C07D 487/06* (2013.01); *Y02E 10/549* (2013.01); *C09K 2211/1044* (2013.01); *H01L 51/5012* (2013.01); *C09B 57/00* (2013.01); *H01L 51/0545* (2013.01)
USPC ....................................................... 544/247

(58) Field of Classification Search
CPC .................................................... C07D 487/06
See application file for complete search history.

(56) References Cited

U.S. PATENT DOCUMENTS

| | | |
|---|---|---|
| 2011/0042651 A1 | 2/2011 | Koenemann et al. |
| 2011/0186821 A1 | 8/2011 | Schaefer et al. |

FOREIGN PATENT DOCUMENTS

| | | |
|---|---|---|
| CN | 101467276 | 6/2009 |
| DE | 1 263 775 | 3/1968 |
| EP | 2489668 A1 * | 8/2012 |
| GB | 1 022 660 | 3/1966 |
| WO | 2010 006890 | 1/2010 |

OTHER PUBLICATIONS

American Chemical Society (ACS). STN Chemical Abstract Service (CAS) RN Database. © 2013.*
International Search Report Issued Jun. 14, 2012 in PCT/IB12/050702 Filed Feb. 16, 2012.
Hans Plümpe et al., "Derivate des 1, 3, 6, 8-Tetraazapyrens mit Virkung Gegen Lamblia-Infektionen", International Congress of Chemotherapy, vol. 5, Jan. 1, 1967, pp. 635-639 with Partial English Translation.
I. V. Borovlev et al., "Diazapyrenes. (Review)", Chemistry of Heterocyclic Compounds, vol. 39, No. 11, 2003, pp. 1417-1442.
Prashant Sonar et al., "1,3,6,8-tetrasubstituted Pyrenes: Solution-Processable Materials for Application in Organic Electronics", Organic Letters, vol. 12, No. 15, 2010, pp. 3292-3295.

* cited by examiner

*Primary Examiner* — Noble Jarrell
*Assistant Examiner* — John S Kenyon
(74) *Attorney, Agent, or Firm* — Oblon, Spivak, McClelland, Maier & Neustadt, L.L.P.

(57) ABSTRACT

Provided are tetraazapyrene compounds of formula (I) and their use as n-type semiconductors. In formula (I), $R^1$, $R^2$, $R^3$, $R^4$, at each occurrence, independently are selected from H, a $C_{1-30}$ alkyl group, a $C_{1-30}$ alkoxy group, a $C_{1-30}$ alkylthio group, a $C_{6-14}$ aryl group, a $C_{6-14}$ aryloxy group, a $C_{6-14}$ arylthio group, a $C_{7-20}$ arylalkyl group, CI and Br; $R^5$, $R^6$, at each occurrence, independently are selected from H, a $C_{1-30}$ alkyl group, a $Cy_{1-30}$ haloalkyl group, a $C_{6-14}$ aryl group and a $C_{7-20}$ arylalkyl group, wherein aryl and arylalkyl can be optionally substituted with one or more halogen, $C_{1-4}$ haloalkyl, —CN, —NO$_2$, —CHO, —COOH, —CONH$_2$, —CO($C_{1-14}$ alkyl), —COO($C_{1-14}$ alkyl), CONHC($C_{1-14}$ alkyl) and —CON($C_{1-14}$ alkyl)$_2$ groups, with the proviso that at least one of $R^1$, $R^2$, $R^3$, $R^4$ is a $C_{6-14}$ aryloxy, a $C_{6-14}$ arylthio I group, CI or Br. (I).

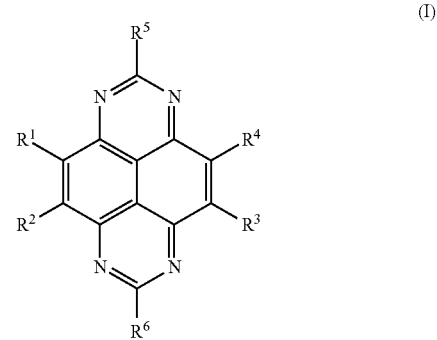

(I)

13 Claims, 4 Drawing Sheets

TETRAAZAPYRENE COMPOUNDS AND THEIR USE AS N-TYPE SEMICONDUCTORS

The invention relates to tetraazapyrene compounds and their use as n-type semiconductors.

Recent developments in organic-based light-emitting diodes (OLEDs), photovoltaics (OPVs), and field-effect transistors (OFETs) have opened up many opportunities in the field of organic electronics. One of the challenges in this field is to develop thin film devices that have environmentally stable electron-transporting (n-type) organic semiconductors with high mobility. The performance and stability of organic n-type materials have significantly lagged behind their p-type counterparts. Some challenges for advancing the technology of organic n-type materials include their vulnerability to ambient conditions (e.g., air) and solution-processability. For example, it is desirable for these materials to be soluble in common solvents so that they can be formulated into inks for inexpensive printing processes.

The most common air-stable n-type organic semiconductors include perfluorinated copper phthalocyanine (CuF$_{16}$Pc), fluoroacyl oligothiophenes (e.g., DFCO-4TCO), N,N'-fluorocarbon-substituted naphthalene diimides (e.g., NDI-F, NDI-XF), cyano-substituted perylene diimides (e.g., PDI-FCN$_2$), and cyano-substituted naphthalene diimides (e.g., NDI-8CN$_2$). See, e.g., Bao et al. (1998), *J. Am. Chem. Soc.*, 120: 207-208; de Oteyza et al. (2005), *Appl. Phys. Lett.*, 87: 183504; Schön et al. (2000), *Adv Mater.* 12: 1539-1542; Ye et al. (2005), *Appl. Phys. Lett.*, 86: 253505; Yoon et al. (2006), *J. Am. Chem. Soc.*, 128: 12851-12869; Tong et al. (2006), *J. Phys. Chem. B.*, 110: 17406-17413; Yuan et al. (2004), *Thin Solid Films*, 450: 316-319; Yoon et al. (2005), *J. Am. Chem. Soc.*, 127: 1348-1349; Katz et al. (2000), *J. Am. Chem. Soc.*, 122: 7787-7792; Katz et al. (2000), *Nature (London)*, 404: 478-481; Katz et al (2001), *Chem. Phys. Chem.*, 3: 167-172; Jung et al. (2006), *Appl. Phys. Lett.*, 88: 183102; Yoo et al. (2006), *IEEE Electron Device Lett.*, 27: 737-739; Jones et al. (2004), *Angew. Chem., Int. Ed. Engl.*, 43: 6363-6366; and Jones et al. (2007), *J. Am. Chem. Soc.*, 129: 15259-15278.

Accordingly, given potential applications in inexpensive and large-area organic electronics that can be produced by high-throughput reel-to-reel manufacture, the art desires new organic n-type semiconducting compounds, especially those possessing desirable properties such as air stability, high charge transport efficiency, and good solubility in common solvents.

In light of the foregoing, it is an object of the present invention to provide compounds that can be utilized as organic semiconductors and related materials, compositions, composites, and/or devices that can address various deficiencies and shortcomings of the state-of-the-art, including those outlined above.

The object is solved by tetraazapyrene compounds of formula I:

(I)

wherein:

$R^1, R^2, R^3, R^4$, at each occurrence, independently are selected from H, a $C_{1-30}$ alkyl group, a $C_{1-30}$ alkoxy group, a $C_{1-30}$ alkylthio group, a $C_{6-14}$ aryl group, a $C_{6-14}$ aryloxy group, a $C_{6-14}$ arylthio group, a $C_{7-20}$ arylalkyl group, Cl and Br, $R^5, R^6$, at each occurrence, independently are selected from H, a $C_{1-30}$ alkyl group, a $C_{1-30}$ haloalkyl group, a $C_{6-14}$ aryl group and a $C_{7-20}$ arylalkyl group, wherein aryl and arylalkyl can be optionally substituted with one or more halogen, $C_{1-4}$ haloalkyl, —CN, —NO$_2$, —CHO, —COOH, —CONH$_2$, —CO(C$_{1-14}$ alkyl), —COO(O$_{1-14}$ alkyl), —CONHC(C$_{1-14}$ alkyl) and —CON(C$_{1-14}$ alkyl)$_2$ groups, with the proviso that at least one of $R^1, R^2, R^3$ and $R^4$ is a $C_{6-14}$ aryloxy, a $C_{6-14}$ arylthio group, Cl or Br.

It has been found that the tetraazapyrene compounds of the present invention have semiconducting activity. Materials prepared from these compounds have demonstrated unexpected properties. It has been discovered that compounds of the present invention can have high carrier mobility and/or good current modulation characteristics in field-effect devices (e.g., thin-film transistors). In addition, it has been discovered that compounds of the present invention can possess certain processing advantages compared to related representative compounds such as better solubility to permit solution-processability and/or good stability at ambient conditions, for example, air stability. Further, the compounds can be embedded with other components for utilization in a variety of semiconductor-based devices.

$R^1, R^2, R^3, R^4, R^5$ and $R^6$ can be a $C_{1-30}$ alkyl group. As used herein, "alkyl" refers to a straight-chain or branched saturated hydrocarbon group. Examples of alkyl groups include methyl, ethyl, propyl (e.g., n-propyl and isopropyl), butyl (e.g., n-butyl, isobutyl, s-butyl, t-butyl), pentyl groups (e.g., n-pentyl, isopentyl, neopentyl), and hexyl (e.g., n-hexyl). An alkyl group can have 1 to 30 carbon atoms, for example 1 to 20 carbon atoms (i.e., $C_{1-20}$ alkyl group). A lower alkyl group typically has up to 4 carbon atoms. Examples of lower alkyl groups include methyl, ethyl, propyl (e.g., n-propyl and isopropyl), and butyl groups (e.g., n-butyl, isobutyl, s-butyl, t-butyl).

$R^5$ and $R^6$ can be a $C_{1-30}$ haloalkyl group. As used herein, "haloalkyl" refers to an alkyl group having one or more halogen substituents. A haloalkyl group can have 1 to 30 carbon atoms, for example 1 to 10 carbon atoms (i.e., $C_{1-10}$ haloalkyl group). Examples of haloalkyl groups include CF$_3$, C$_2$F$_5$, CHF$_2$, CH$_2$F, CCl$_3$, CHCl$_2$, CH$_2$Cl, C$_2$Cl$_5$, and the like. Perhaloalkyl groups, i.e., alkyl groups wherein all of the hydrogen atoms are replaced with halogen atoms (e.g., CF$_3$ and C$_2$F$_5$), are included within the definition of "haloalkyl." For example, a $C_{1-20}$ haloalkyl group can have the formula —C$_a$H$_{2a+1-b}$X$_b$, wherein X, at each occurrence, is F, Cl, Br, or I, a is an integer in the range of 1 to 20, and b is an integer in the range of 1 to 41, provided that b is not greater than 2a+1.

Preferred haloalkyl groups are $C_{1-6}$ haloalkyl groups, in particular $C_{1-4}$ haloalkyl groups. Particularly preferred are haloalkyl groups containing one or more fluorine substituents. Examples of particular haloalkyl groups are —CF$_3$, —C$_2$F$_5$, —C$_3$F$_7$, —C$_4$F$_9$ and —CH$_2$C$_3$F$_7$.

$R^1, R^2, R^3, R^4, R^5$ and $R^6$ can be an aryl group having from 6 to 14 carbon atoms. As used herein, "aryl" refers to an aromatic monocyclic hydrocarbon ring system or a polycyclic ring system in which two or more aromatic hydrocarbon rings are fused together or at least one aromatic monocyclic hydrocarbon ring is fused to one or more cycloalkyl and/or cycloheteroalkyl rings. Examples of aryl groups having only aromatic carbocyclic ring(s) include, but are not limited to, phenyl, 1-naphthyl, 2-naphthyl, anthracenyl, phenanthrenyl and like groups. Examples of polycyclic ring systems in which at least one aromatic carbocyclic ring is fused to one or more cycloalkyl or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include, but are not limited to, benzodioxanyl, benzodioxolyl, chromanyl, indolinyl groups, and the like. In certain embodiments, the aryl group is an aryl group substituted with another aryl groups and can be referred to as a biaryl group. Examples of biaryl groups are a biphenyl group and a terphenyl group. In certain embodiments, the aryl group is a phenyl group.

$R^5$ and $R^6$ can be aryl groups, as defined above, substituted with one or more, e.g. 1 to 5 electron-withdrawing groups independently selected from halogen, —CN, —NO$_2$, —CF$_3$, —OCF$_3$, —CO$_2$(C$_{1-14}$ alkyl), —CHO, C$_1$-C$_{14}$ alkylsulfon, C$_{6-14}$ arylsulfon, a sulfonic acid C$_{1-14}$ alkylester or —C$_{6-14}$ arylester group, —CONH(C$_{1-14}$ alkyl) and —CON(C$_{1-14}$ alkyl)$_2$. In some preferred embodiments, the electron withdrawing group is halogen, —COO(C$_{1-14}$ alkyl), —CN, —NO$_2$, —CF$_3$, or —OCF$_3$. In certain embodiments, the electron withdrawing group is F, Cl, Br, I, or —CN.

In certain embodiments, the aryl group is a phenyl group substituted with 1 to 5 halogen atoms. In some preferred embodiments, $R^5$, $R^6$ is a phenyl group substituted with 1 to 5 F atoms. In some embodiments, the aryl group is perhalogenated, i.e. all of the hydrogen atoms are replaced with halogen, in particular with F. One preferred perhalogenated aryl group is pentafluorophenyl.

$R^1$, $R^2$, $R^3$, $R^4$, $R^5$ and $R^6$ can be arylalkyl groups having from 7 to 20 carbons atoms. The aryl group bound in the arylalkyl group can be an (optionally substituted) aryl group having from 6 to 14 carbon atoms, as defined herein, linked via an alkylene group, in general an C$_{1-6}$ alkylene group, to the tetraazapyrene core. Examples of arylalkyl groups are benzyl, phenylethyl and phenylpropyl.

$R^5$ and $R^6$ can be an arylalkyl group substituted with one or more electron withdrawing groups selected from halogen, —COO(C$_{1-14}$ alkyl), —CN, —NO$_2$, —CF$_3$, or —OCF$_3$. In certain embodiments, the electron withdrawing group is F, Cl, Br, I, or —CN, in particular F. The arylalkyl group can be perhalogenated, i.e. all of the hydrogen atoms are replaced with halogen, in particular with F.

$R^1$, $R^2$, $R^3$, $R^4$ can be an alkoxy group having from 1 to 30 carbon atoms, preferably from 1 to 10 carbon atoms. More preferred are C$_{1-6}$ alkoxy groups including methoxy, ethoxy, propyloxy (e.g., n-propyloxy and isopropyloxy), butyloxy (e.g., n-butyloxy, isobutyloxy, s-butyloxy, t-butyloxy), pentyloxy groups (e.g., n-pentyloxy, isopentyloxy, neopentyloxy), and hexyloxy (e.g., n-hexyloxy).

$R^1$, $R^2$, $R^3$, $R^4$ can be an alkylthio group having from 1 to 30 carbon atoms, preferably 1 to 10 carbon atoms. More preferred are C$_{1-6}$ alkylthio groups including methylthio, ethylthio, propylthio (e.g., n-propylthio and isopropylthio), butylthio (e.g., n-butylthio, isobutylthio, s-butylthio, t-butylthio), pentylthio groups (e.g., n-pentylthio, isopentylthio, neopentylthio), and hexylthio (e.g., n-hexylthio).

$R^1$, $R^2$, $R^3$, $R^4$ can be an aryloxy group having from 6 to 14 carbon atoms. The aryloxy group —O-aryl can contain C$_{6-14}$ aryl groups as defined herein. Preferred aryloxy group is a phenoxy group.

The aryloxy group can be substituted with one or more, e.g. 1 to 5, C$_{1-10}$ alkyl groups, in particular C$_{1-4}$ alkyl groups, F, Cl, Br, CN, and CF$_3$.

$R^1$, $R^2$, $R^3$, $R^4$ can be an arylthio group having from 6 to 14 carbon atoms. The arylthio group —S-aryl can contain C$_{6-14}$ aryl groups as defined herein. Preferred arylthio groups are a phenylthio group.

The arylthio group can be substituted with one or more, e.g. 1 to 5, C$_{1-10}$ alkyl groups, in particular C$_{1-4}$ alkyl groups, F, Cl, Br, CN, and CF$_3$.

The chloro- or bromo-substituted tetrazapyrenes can be obtained from the tetraazapyrenes of formula (II) by chlorination or bromination using a chlorination or bromination agent.

(II)

In one preferred embodiment, $R^1$ and $R^3$ are Cl or Br, and $R^2$ and $R^4$ are hydrogen. The 4,9-dichloro- or dibromotetraazapyrenes can be obtained from the tetraazapyrenes of formula (II) using as chlorination agent N,N'-dichloroisocyanuric and as bromination agent N,N'-dibromoisocyanuric acid, according to Reaction Scheme a:

Scheme a

In one preferred embodiment, $R^1$-$R^4$ are Cl or Br. The 4,5,9,10-tetrachlorotetraazapyrenes can be obtained from tetraazapyrenes of formula (II) by using dichloroisocyanuric acid as the chlorination agent.

The 4,5,9,10-tetrabromotetraazapyrenes can be obtained by using molecular bromine in concentrated sulfuric acid as the bromination agent according to Scheme b.

$FeCl_3$ and $FeBr_3$, respectively, can be added as catalysts.

Scheme b 2,7-substituted tetraazapyrenes of formula (II) can be obtained from 1,4,5,8-tetraaminonaphthalene-hexachlorostannate and an carboxylic acid anhydride containing residues $R^5$ or $R^6$ bound to the anhydride group, according to Reaction Scheme c:

Scheme c

Suitable carboxylic acid anhydrides are pentafluorobenzoic acid anhydride and perfluoroalkane carboxylic acid anhydrides containing perfluoro-alkyl groups with 1 to 6 carbon atoms.

Aryloxy- and arylthio-substituted tetraazapyrenes can be obtained form chloro- or bromo-substituted tetraazapyrenes by substitution of chlorine or bromine using an aromatic hydroxy or mercapto compound, such as (optionally substituted) phenol, thiophenol, naphthol and thionaphthol.

In one preferred embodiment, $R^1$-$R^4$ are thioaryl groups, in particulat thiophenyl groups.

For example, 4,5,9,10-tetrathiophenyl tetraazapyrene can be obtained from the corresponding tetrabromo compound according to Reaction Scheme d:

Scheme d

Alkoxy- and alkylthio-substituted tetraazapyrenes can be obtained form chloro- or bromo-substituted tetraazapyrenes by substitution of chlorine or bromine using alkali alkoxide and alkali thioalkoxide, such as sodium methoxide, sodium ethoxide, or potassium n-butoxide.

Aryl-substituted tetraazapyrenes can be obtained form chloro- or bromo-substituted tetraazapyrenes by substitution of chlorine or bromine using the corresponding arylboronic acid, such as phenylboronic acid.

As the compounds disclosed herein are soluble in common solvents, the present invention can offer processing advantages in fabricating electrical devices such as thin film semiconductors, field-effect devices, organic light emitting diodes (OLEDs), organic photovoltaics, photodetectors, capacitors, and sensors. As used herein, a compound can be considered soluble in a solvent when at least 1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methylpyrrolidone. Examples of common inorganic solvents include water and ionic liquids.

Accordingly, the present invention further provides compositions that include one or more compounds disclosed herein dissolved or dispersed in a liquid medium, for example, an organic solvent, an inorganic solvent, or combinations thereof (e.g., a mixture of organic solvents, inorganic solvents, or organic and inorganic solvents). In some embodiments, the composition can further include one or more additives independently selected from detergents, dispersants, binding agents, compatiblizing agents, curing agents, initiators, humectants, antifoaming agents, wetting agents, pH modifiers, biocides, and bactereriostats. For example, surfactants and/or other polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, such compositions can include one or more compounds disclosed herein, for example, two or more different compounds of the present invention can be dissolved in an organic solvent to prepare a composition for deposition. In certain embodiments, the composition can include two or more regioisomers. Further, it should be understood that the devices described herein also can comprise one or more compounds of the present invention, for example, two or more regioisomers as described herein.

Various deposition techniques, including various solution-processing techniques, have been used in preparing organic electronics. For example, much of the printed electronics technology has focused on inkjet printing, primarily because this technique offers greater control over feature position and multilayer registration. Inkjet printing is a noncontact process, which offers the benefits of not requiring a preformed master (compared to contact printing techniques), as well as digital control of ink ejection, thereby providing drop-on-demand printing. Micro dispensing is another non-contact method of printing. However, contact printing techniques have the key advantage of being well-suited for very fast roll-to-roll processing. Exemplary contact printing techniques include, but are not limited to, screen-printing, gravure printing, offset printing, flexographic printing, lithographic printing, pad printing, and microcontact printing. As used herein, "printing" includes a noncontact process, for example, inkjet printing, micro dispensing, and the like, and a contact process, for example, screen-printing, gravure printing, offset printing, flexographic printing, lithographic printing, pad printing, microcontact printing, and the like. Other solution processing techniques include, for example, spin coating, drop-casting, zone casting, dip coating, blade coating, or spraying. In addition, the deposition step can be carried out by vacuum vapor-deposition.

The present invention, therefore, further provide methods of preparing a semiconductor material. The methods can include preparing a composition that includes one or more compounds disclosed herein dissolved or dispersed in a liquid medium such as a solvent or a mixture of solvents, and depositing the composition on a substrate to provide a semiconductor material (e.g., a thin film semiconductor) that includes one or more compounds disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatiblizing agents, curing agents, initiators, humectants, antifoaming agents, wetting agents, pH modifiers, biocides, and bactereriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices such as field effect transistors (e.g., thin film transistors), photovoltaics, organic light emitting diodes (OLEDs), complementary metal oxide semiconductors (CMOSs), complementary inverters, D flip-flops, rectifiers, and ring oscillators, that make use of the compounds and the semiconductor materials disclosed herein also as well as methods of making the same are within the scope of the present invention.

Accordingly, the present invention provides articles of manufacture such as the various devices described herein that include a composite having a semiconductor material of the present invention, a substrate component, and/or a dielectric component. The substrate component can be selected from materials including doped silicon, an indium tin oxide (ITO), ITO-coated glass, ITO-coated polyimide or other plastics, aluminum or other metals alone or coated on a polymer or other substrate, a doped polythiophene or other polymers, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., described in Yoon, M-H. et al., *PNAS*, 102 (13): 4678-4682 (2005), the entire disclosure of which is incorporated by reference herein), and hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be incorporated within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Figure 4:
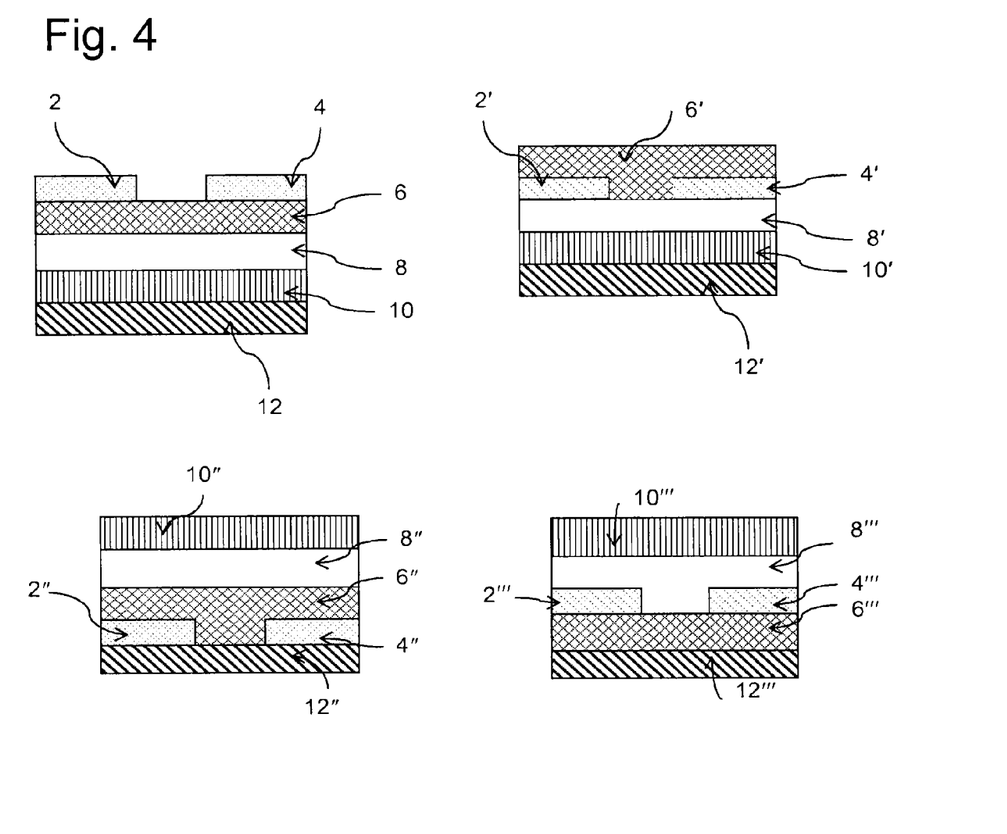

An aspect of the present invention, therefore, relates to methods of fabricating an organic field effect transistor that incorporates a semiconductor material of the present invention. The semiconductor materials of the present invention can be used to fabricate various types of organic field effect transistors including top-gate top-contact capacitor structures, top-gate bottom-contact capacitor structures, bottom-gate top-contact capacitor structures, and bottom-gate bottom-contact capacitor structures. FIG. 4 illustrates the four common types of OFET structures: top-contact bottom-gate structure (top left), bottom-contact bottom-gate structure (top right), bottom-contact top-gate structure (bottom left), and top-contact top-gate structure (bottom right). As shown in FIG. 4, an OFET can include a dielectric layer (e.g., shown as 8, 8', 8", and 8'"), a semiconductor layer (e.g., shown as 6, 6', 6", and 6'"), a gate contact (e.g., shown as 10, 10', 10", and 10'"), a substrate (e.g., shown as 12, 12', 12", and 12'"), and source and drain contacts (e.g., shown as 2, 2', 2", 2'", 4, 4', 4", and 4'").

In certain embodiments, OTFT devices can be fabricated with the present compounds on doped silicon substrates, using SiO$_2$ as the dielectric, in top-contact geometries. In particular embodiments, the active semiconducting layer which incorporates at least a compound of the present invention can be deposited by vacuum vapor deposition at room temperature or at an elevated temperature. In other embodiments, the active semiconducting layer which incorporates at least a compound of the present invention can be applied by solution-based process, for example, spin-coating or jet printing. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a compound of the present invention can be deposited at room temperature or at an elevated temperature. In other embodiments, the active semiconducting layer which incorporates at least a compound of the present invention can be applied by spin-coating or printing as described herein. Gate and source/drain contacts can be made of Au, other metals, or conducting polymers and deposited by vapor-deposition and/or printing.

Other articles of manufacture in which compounds of the present invention are useful are photovoltaics or solar cells. Compounds of the present invention can exhibit broad optical absorption and/or a very positively shifted reduction potential making them desirable for such applications. Accordingly, the compounds described herein can be used as an n-type semiconductor in a photovoltaic design, which includes an adjacent p-type semiconducting material that forms a p-n junction. The compounds can be in the form of a thin film semiconductor, which can be a composite of the thin film semiconductor deposited on a substrate. Exploitation of compounds of the present invention in such devices is within the knowledge of the skilled artisan.

Accordingly, another aspect of the present invention relates to methods of fabricating an organic light-emitting transistor, an organic light-emitting diode (OLED), or an organic photovoltaic device that incorporates one or more semiconductor materials of the present invention.

The following examples are provided to illustrate further and to facilitate understanding of the present invention and are not in any way intended to limit the invention.

EXAMPLES

Example 1

Preparation of 2,6-bis-(trifluoromethyl)-tetraazapyrene n = 1,2,3

1.5 g (2.88 mmol) 1,4,5,8-tetraminonaphthalene hexachlorostannate were suspended under argon atmosphere in 30 ml of anhydrous tetrahydrofurane. After addition of 1 ml anhydrous triethylamine, 5 ml (35 mmol) of trifluoro acetic acid anhydride were slowly added while cooling with ice. The reaction mixture was stirred for 72 h at 70° C. After cooling to room temperature, the reaction solution was filtrated, the filtrate was concentrated in vacuo, and the raw product was re-crystallized 3 times from methanol. 610 mg (1.78 mmol, 62%) of beige, crystalline solid were obtained.

$^1$H-NMR (600 MHz, CDCl$_3$): δ=8.92 (s, 4H).

Examples 2 and 3

Preparation of 2,7-bis-(pentafluoroethyl)-tetraazapyrene (Example 2) and 2,7-bis(heptafluoropropyl)-tetraazapyrene (Example 3)

1 g (1.9 mmol) of 1,4,5,8-tetraminonaphthalene hexachlorstannate were suspended under argon atmosphere in 30 ml anhydrous tetrahydrofurane. After addition of about 0.5 ml anhydrous triethylamine, 7.9 mmol of the corresponding carboxylic acid anhydride (pentafluoroethyl carbocylic acid anhydride and heptafluoropropyl carbocylic acid anhydride, respectively) were slowly added while cooling with ice. The reaction mixture was stirred for 72 h at 70° C. After cooling to room temperature, the reaction solution was filtered, and the filtrate was concentrated in vacuo. The raw product was purified by column chromatography (silica gel, hexane/acetic acid ester 4:1) and re-crystallized from methanol.

290 mg (0.66 mmol, 45%) beige, crystalline solid were obtained in case of 2,7-bis(pentafluoroethyl)-tetraazapyrene.

$^1$H-NMR (600 MHz, CDCl$_3$): δ=8.90 (s, 4H)

280 mg (0.52 mmol, 36%) of beige, crystalline solid were obtained in case of 2,7-bis(heptafluoropropyl)-tetraazapyrene.

$^1$H-NMR (600 MHz, CDCl$_3$): δ=8.94 (s, 4H)

Example 4

Preparation of 2,7-bis-(pentafluorophenyl)-tetraazapyrene 704 mg (1.35 mmol) 1,4,5,8-tetraminonaphthalene hexachlorostannate were suspended in 20 ml of anhydrous tetrahydrofurane. To the suspension, 1 ml of anhydrous triethylamine was added. 3.31 g (8.16 mmol) of 2,3,4,5,6-pentafluorobenzoic acid anhydride were added, and the obtained reaction mixture was stirred for 72 h at 70° C. under argon atmosphere. The product was purified by column chromatography (silica gel; pentane/acetic acid ester 3:1). 322 mg (44%) of light yellow solid were obtained.

$^1$H-NMR (600 MHz, CDCl$_3$): δ=8.78 (s, 4H)

The charge carrier mobility was determined to be μ=0.002 cm$^2$/Vs

Example 5

Preparation of 2,7-bis-(pentafluorophenyl)-4,5,9,10-tetrabromotetraazapyrene

To a solution of 60 mg (0.11 mmol) 2,7-pentafluorophenyl-1,3,6,8-tetraazapyrene in 20 ml concentrated sulfuric acid were added 1 ml of bromine. The solution was stirred at 90° C. for 4 h. The reaction solution was cooled to room temperature and poured on ice and neutralized with NaOH. The product precipitated as white solid. The yield was 15 mg (16%).

The charge carrier mobility was determined to be μ=0.0006 cm$^2$/Vs.

Example 6

Preparation of 2,7-bis-(perfluoroalkyl)-4,9-dibromotetraazypyrene 0.50 mmol of the corresponding perfluoroalkyl-1,3,6,8-tetraazapyrene were dissolved in 50 ml concentrated sulfuric acid. 861 mg (3.0 mmol) of dibromoisocyanuric acid were added. The reaction mixture was stirred overnight in a dark room at room temperature. The reaction solution was poured on ice, neutralized with NaOH, and the reaction product extracted with CHCl$_3$. The reaction product was obtained as white solid.

| | reaction batch [mg] | yield | $^1$H-NMR (600 MHz, CDCL$_3$) | charge carrier mobility |
|---|---|---|---|---|
| n = 1 | 171 mg | 50 mg (20%) | δ = 9.24 (2, 2H) | 0.00065 cm$^2$/VS |
| n = 2 | 221 mg | 51 mg (17%) | δ = 9.26 (2, 2H) | n.d. |
| n = 3 | 271 mg | 56 mg (16%) | δ = 9.26 (2, 2H) | 0.003 cm$^2$/Vs |

Example 7

Preparation of 4,5,9,10-tetraphenylthiotetraazapyrene 100 mg (0.19 mmol) 4,5,9,10-tetrabromo-1,3,6,8-tetraazypyrene, 21 mg (0,057 mmol) of cetyltrimethylammonium bromide and 619 mg (1.90 mmol) of cesium carbonate were suspended in 4 ml aqua dest. and 20 ml mesitylene. 126 mg (1.14 mmol) of thiophenol were slowly added, and the reaction mixture was stirred under argon atmosphere for 48 h at 80° C. After cooling to room temperature, the precipitated reaction product was separated by centrifugation, washed with ethanol and pentane, and dried in vacuo. 30 mg (25%) of a red solid were obtained.

$^1$H-NMR (600 MHz, CDCl$_3$): δ=9.71 (s, 2H, N—CH—N), 7.14-7.18 (m, 12G, H$_{aryl}$), 7.30 (m, 8H, H$_{aryl}$)

Example 8

Preparation of 2,7-bis-(trifluoromethyl)-4,5,9,10-tetrachloro-1,3,6,8-tetraazapyrene To a solution of 50 mg (0.15 mmol) of 2,7-bis-(trifluoromethyl)-1,3,6,8-tetraazapyrene in 10 ml concentrated sulfuric acid were added 300 mg (1.5 mmol) of dichloroisocyanuric acid in the dark. The reaction solution was stirred for 10 days at 100° C., poured on ice, and neutralized with aqueous NaOH. The aqueous solution was extracted repeatedly with dichloromethane, the unified organic phases dried over magnesium sulfate, and the solvent removed in vacuo. After repeated re-crystallization from methanol and tetrahydrofurane, 15 mg (0.03 mmol, 20%) of a colourless solid were isolated.

$^{19}$F-NMR (376.27 MHz, CDCl$_3$, 295 K)
δ=68.62 (s, CF$_3$)

Example 9

Preparation of 2,7-bis-trifluoromethyl-4,5,9,10-tetrachloro-1,3,6,8-tetraazapyrene To a stirred solution of 50 mg (0.15 mmol) 2,7-bis-trifluoromethyl-1,3,6,8-tetraazapyrene in 10 ml concentrated sulfuric acid were added 300 mg (1.50 mmol) dichloroisocyanuric acid. The reaction mixture was stirred at 100° C. for 10 days under the exclusion of light and then poured onto ice. The resulting solution was neutralized with sodium hydroxide and extracted with dichloromethane. After evaporation of the solvent the solid was recrystallized from THF and methanol to yield 15 mg (0.03 mmol, 20%) of a colorless solid.

$^{13}$C-NMR (150.92 MHz, CDCl$_3$): δ=157.0 (q, $^2J_{CF}$=38.7 Hz, C$^7$), 151.6 (s, C$^{1/4}$), 141.5 (C$^{2/3}$Cl), 119.5 (q, $^1J_{CF}$=275.6 Hz, CF$_3$), 111.8 (C$^{5/6}$).
$^{19}$F-NMR (376.27 MHz, CDCl$_3$): δ=−68.62 (s, CF$_3$).

Example 10

Preparation of 4,9-bis-(4-cyanophenyl)-1,3,6,8-tetraazapyrene

An oven-dried Schlenk tube was loaded with 100 mg (0.20 mmol) 2,7-bis-(trifluoromethyl)-4,9-dibromo-1,3,6,8-tetraazapyrene, 147 mg (1.00 mmol) 4-cyanophenylboronic acid, 391 mg (1.20 mmol) caesium carbonate and 15 mg (0.02 mmol) Pd(dppf)Cl$_2$ and evacuated and refilled with argon for three times. 20 ml abs. 1,4-dioxane were added, the Schlenk tube was sealed with a glass cap and the reaction mixture was stirred at 101° C. for 48 h. The mixture was allowed to cool to room temperature, the solvent was evaporated and the solid residue was extracted with chloroform. The organic phase was washed with water and brine, dried over sodium sulphate and evaporated in vacuo. The solid was washed with methanol and pentane to yield 65 mg (0.12 mmol, 60%) of the compound as a light grey solid.

$^1$H-NMR (600.13 MHz, CDCl$_3$): δ=9.02 (s, 2H, C$^3$H), 8.14 (d, 4H, $^3J_{HH}$=8.1 Hz), 7.98 (d, 4H, $^3J_{HH}$=8.2 Hz).

$^{13}$C-NMR (150.90 MHz, CDCl$_3$): δ=156.2 (C$^7$), 153.7 (C$^4$), 151.9 (C$^1$), 147.1 (C$^2$), 138.7 (C$^8$), 136.4 (C$^3$), 132.5 (C$^{10}$), 131.5 (C$^9$), 118.2 (CN), 114.3 (C$^{5/6}$), 114.0 (C$^{11}$).

$^{19}$F-NMR (79 MHz, CDCl$_3$): δ=−68.76 (s, 6F, CF$_3$).

Example 11

Preparation of 4,9-bis-(4-trifluoromethylphenyl)-1,3,6,8-tetraazapyrene

An oven-dried Schlenk tube was loaded with 130 mg (0.26 mmol) 2,7-bis-(trifluoromethyl)-4,9-dibromo-1,3,6,8-tetraazapyrene, 197 mg (1.04 mmol) 4-trifluoromethylphenylboronic acid, 508 mg (1.56 mmol) caesium carbonate and 19 mg (0.03 mmol) Pd(dppf)Cl$_2$ and evacuated and refilled with argon for three times. 20 ml abs. 1,4-dioxane were added, the Schlenk tube was sealed with a glass cap and the reaction mixture was stirred at 101° C. for 48 h. The mixture was allowed to cool to room temperature, the solvent was evaporated and the solid residue was extracted with chloroform. The organic phase was washed with water and brine, dried over sodium sulphate and evaporated in vacuo. The solid was washed with methanol and pentane to yield 35 mg (0.06 mmol, 23%) of the compound as a white solid.

$^1$H-NMR (600.13 MHz, CDCl$_3$): δ=9.02 (s, 2H, C$^3$H), 8.20 (d, 4H, $^3J_{HH}$=8.0 Hz), 7.95 (d, 4H, $^3J_{HH}$=8.1 Hz).

$^{13}$C-NMR (150.90 MHz, CDCl$_3$): δ=156.1 (q, $^2J_{CF}$=37.2 Hz, C$^7$), 153.8 (C$^4$), 152.3 (C$^1$), 147.7 (C$^2$), 137.9 (C$^8$), 136.2 (C$^3$), 132.1 (q, $^2J_{CF}$=33.0 Hz, C$^{11}$), 131.3 (C$^9$), 125.8 (C$^{10}$), 124.8 (C$^{12}$F$_3$), 119.0 (CF$_3$), 114.2 (C$^{5/6}$).

$^{19}$F-NMR (79 MHz, CDCl$_3$): δ=−68.76 (s, 6F, CF$_3$), −62.72 (s, 6F, C$^{12}$F$_3$).

Example 12

Fabrication of Vapor-Deposited OFETs

General procedure for the fabrication of vapor-deposited OFETs in the top-contact configuration.

Highly doped p-type silicon (100) wafers (0.01-0.02 Ω·cm) were used as substrates A. Onto substrates A, a 30 nm thick layer of aluminum is deposited by thermal evaporation in a Leybold UNIVEX 300 vacuum evaporator from a tungsten wire, at a pressure of 2×10$^{-6}$ mbar and with an evaporation rate of 1 nm/s. The surface of the aluminum layer is oxidized by a brief exposure to an oxygen plasma in an Oxford reactive ion etcher (RIE, oxygen flow rate: 30 sccm, pressure: 10 mTorr, plasma power: 200 W, plasma duration 30 sec) and the substrate is then immersed into a 2-propanol solution of a phosphonic acid (1 mMol solution of C$_{14}$H$_{29}$PO(OH)$_2$ [TDPA] or 1 mMol solution of C$_7$F$_{15}$C$_{11}$H$_{22}$PO(OH)$_2$ [FODPA]) and left in the solution for 1 hour, which results in the formation of a self-assembled monolayer (SAM) of phosphonic acid molecules on the aluminum oxide surface. The substrate is taken out of the solution and rinsed with pure 2-propanol, dried in a stream of nitrogen and left for 10 min on a hotplate at a temperature of 100° C. The total capacitance of the AlO$_x$/SAM gate dielectric on substrate A is 810 nF/cm$^2$ in case of C$_{14}$H$_{29}$PO(OH)$_2$ and 710 nF/cm$^2$ in case of C$_7$F$_{15}$C$_{11}$H$_{22}$PO(OH)$_2$.

The contact angle of water on the TDPA-treated substrates is 108°, and on the FODPA-treated substrates 118°.

A 30 nm thick film of the organic semiconductor is deposited by thermal sublimation in a Leybold UNIVEX 300 vacuum evaporator from a molybdenum boat, at a pressure of 2×10$^{-6}$ mbar and with an evaporation rate of 0.3 nm/s. For the source and drain contacts 30 nm of gold is evaporated through a shadow mask in a Leybold UNIVEX 300 vacuum evaporator from tungsten boat, at a pressure of 2×10$^{-6}$ mbar and with an evaporation rate of 0.3 nm/s. The transistors have a channel length (L) ranging from 10 to 100 μm and a channel width (W) ranging from 50 to 1000 μm. To be able to contact the back side of the silicon wafer, the wafer (which also serves as the gate electrode of the transistors) is scratched on the back side and coated with silver ink.

The electrical characteristics of the transistors are measured on a Micromanipulator 6200 probe station using an Agilent 4156C semiconductor parameter analyzer. All measurements are performed in air at room temperature. The probe needles are brought into contact with the source and drain contacts of the transistors by putting them down carefully on top of the gold contacts. The gate electrode is contacted through the metal substrate holder onto which the wafer is placed during the measurements.

To obtain the transfer curve the drain-source voltage (V$_{DS}$) is held to 3 V. The gate-source voltage V$_{GS}$ is swept at medium speed from 0 to 3 V in steps of 0.03 V and back. The charge-carrier mobility is extracted in the saturation regime from the slope of (I$_D$)$^{1/2}$ versus V$_{GS}$.

To obtain the output characteristics the drain-source voltage (V$_{DS}$) is swept at medium speed from 0 to 3 V in steps of 0.03 V, while the gate-source voltage V$_{GS}$ is held at up to 8 different voltages (e.g. 0, 0.5, 1, 1.5, 2, 2.5, 3 V). The results are summarized in table 1.

Figure 1A:
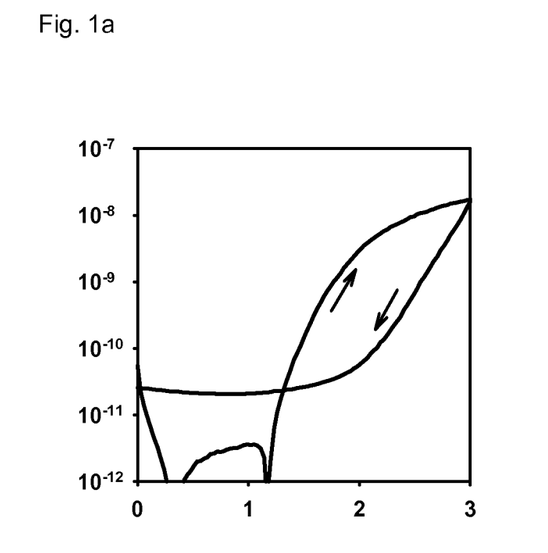
Figure 1B:
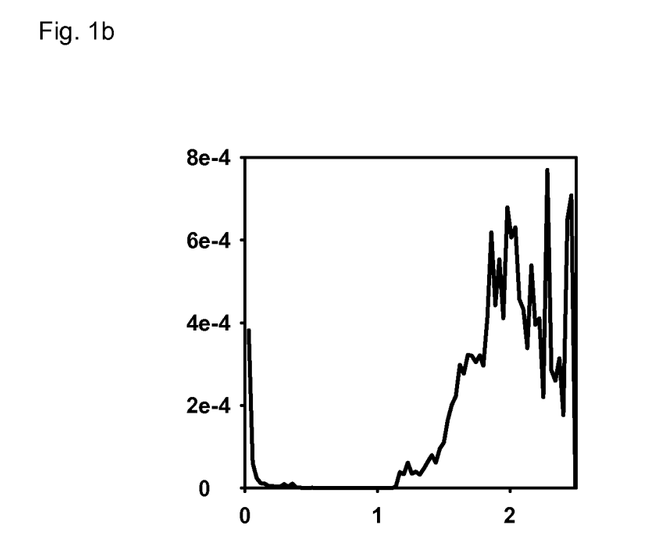

FIG. 1a, 1b show the output characteristics and transfer curve of the compound of Example 6 (n=1). In FIG. 1a, the drain current in A is plotted against the gate-source voltage in V. In FIG. 1b, the electron mobility in cm$^2$/Vs is plotted against the gate-source voltage in V. The drain-source voltage was 2.0 V.

Figure 2A:
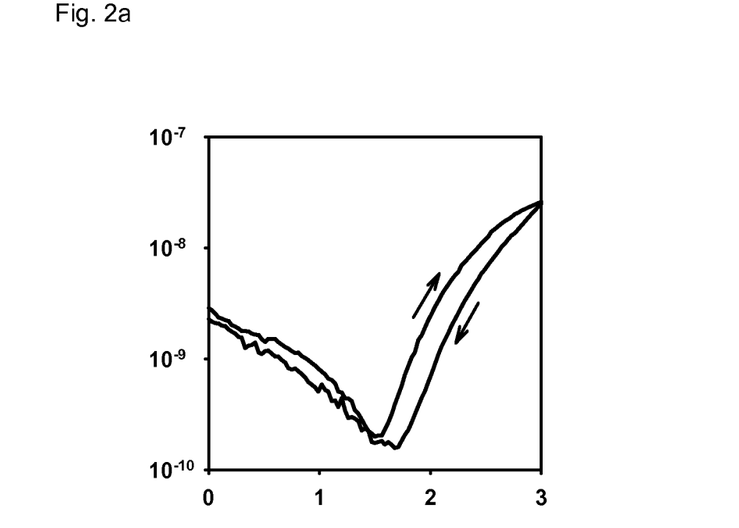
Figure 2B:
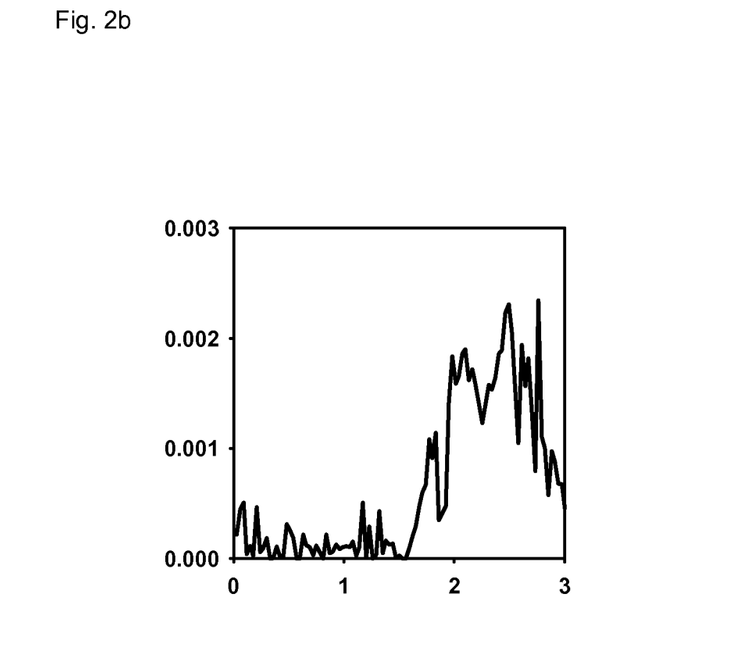

FIG. 2a, 2b show the output characteristics and transfer curve of the compound of Example 4. In FIG. 2a, the drain current in A is plotted against the gate-source voltage in V. In FIG. 2b, the electron mobility in cm$^2$/Vs is plotted against the gate-source voltage in V. The drain-source voltage was 2.0 V.

Figure 3A:
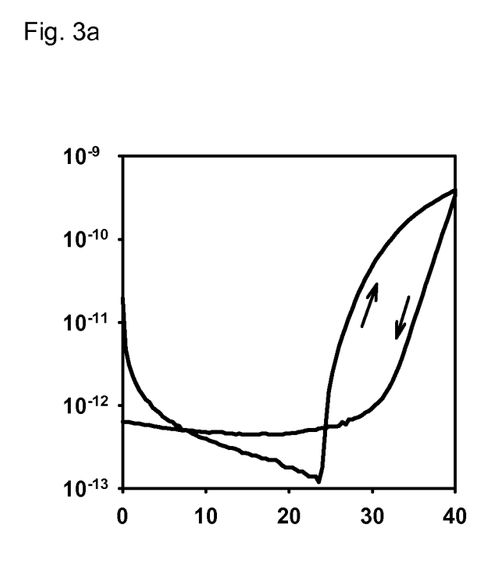
Figure 3B:
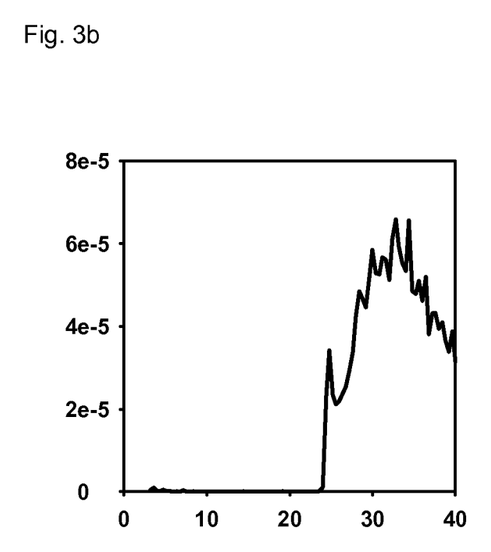

FIG. 3a, 3b show the output characteristics and transfer curve of the compound of Example 5. In FIG. 3a, the drain current in A is plotted against the gate-source voltage in V. In

FIG. 3b, the electron mobility in cm²/Vs is plotted against the gate-source voltage in V. The drain-source voltage was 40 V.

Table 1 gives the field-effect mobilities (μ) and on/off ratios ($I_{on}/I_{off}$) for compounds of examples 6 (n=1, n=3), 4, and 5 at various substrate temperatures ($T_{sub}$) measured in ambient air.

| Compound from example | Substrate | Substrate temperature $T_{sub}$ [° C.] | Electron mobility μ [cm²/Vs] | On/off ratio $I_{on}/I_{off}$ |
|---|---|---|---|---|
| 6 (n = 1) | A | 20 | $6.5 \cdot 10^{-4}$ | $10^3$ |
| 6 (n = 3) | A | 20 | $3 \cdot 10^{-3}$ | $10^4$ |
| 4 | A | 20 | $2 \cdot 10^{-3}$ | $10^2$ |
| 5 | B | 50 | $6 \cdot 10^{-5}$ | $10^3$ |

The invention claimed is:

1. A tetraazapyrene compound of formula (I):

wherein:
$R^1$ and $R^3$ are Cl or Br and $R^2$ and $R^4$ are H; or
$R^1$, $R^2$, $R^3$, and $R^4$ are Cl or Br; or
$R^1$, $R^2$, $R^3$, and $R^4$ are a $C_{6-14}$ aryloxy or a $C_{6-14}$ arylthio;
$R^5$ and $R^6$ are each independently H, a $C_{1-30}$ alkyl, a $C_{1-30}$ haloalkyl, an optionally halogen-substituted $C_{6-14}$ aryl, and an optionally halogen-substituted $C_{7-20}$ arylalkyl.

2. The compound according to claim 1, wherein $R^5$ and $R^6$ are a $C_{1-10}$ haloalkyl.

3. The compound according to claim 2, wherein $R^5$ and $R^6$ are a $C_{1-6}$ perfluoroalkyl.

4. The compound according to claim 1, wherein $R^5$ and $R^6$ are a $C_{6-14}$ aryl or a $C_{7-20}$ arylalkyl which are each substituted with one or more halogen atoms.

5. The compound according to claim 4, wherein $R^5$ and $R^6$ are a phenyl substituted with from 1 to 5 fluorine atoms.

6. A process for producing the compound of claim 1, the process comprising:
chlorinating or brominating a tetraazapyren of formula (II):

with a chlorination or bromination agent,
wherein, in formula (II), $R^5$ and $R^6$ are the same and are selected from a H, a $C_{1-30}$ alkyl, a $C_{1-30}$ haloalkyl, an optionally halogen-substituted $C_{6-14}$ aryl, and an optionally halogen-substituted $C_{7-20}$ arylalkyl and
wherein, in formula (I), $R^1$, $R^2$, $R^3$, and $R^4$ are H, Cl, or Br.

7. The process according to claim 6, wherein, in formula (I), $R^1$ and $R^3$ are Cl or Br, and $R^2$ and $R^4$ are H, and
wherein the chlorination agent if present is N,N'-dichloroisocyanuric acid, and the bromination agent if present is N,N'-dibromoisocyanuric acid.

8. The process according to claim 6, wherein the tetraazapyrene of formula (II) is obtained by a process comprising:
reacting tetraminonaphthalene hexachlorostannate with a carboxylic acid anhydride of formula (III)

thereby obtaining the tetraazapyrene of formula (II),
wherein, in formula (III), $R^5$ and $R^6$ are the same and are selected from a H, a $C_{1-30}$ alkyl, a $C_{1-30}$ haloalkyl, an optionally halogen-substituted $C_{6-14}$ aryl, and an optionally halogen-substituted $C_{7-20}$ arylalkyl.

9. A thin film semiconductor comprising the compound of claim 1.

10. A field effect transistor device comprising the thin film semiconductor of claim 9.

11. A photovoltaic device comprising the thin film semiconductor of claim 9.

12. An organic light emitting diode device comprising the thin film semiconductor of claim 9.

13. A unipolar or complementary circuit device comprising the thin film semiconductor of claim 9.

* * * * *